US008858524B2

(12) United States Patent
Damaghi et al.

(10) Patent No.: US 8,858,524 B2
(45) Date of Patent: Oct. 14, 2014

(54) SKIN FRIENDLY DIAPER

(75) Inventors: Babak Damaghi, Kings Point, NY (US); Hamzeh Karami, Brewster, MA (US)

(73) Assignee: First Quality Products, Inc., Great Neck, NY (US)

( * ) Notice: Subject to any disclaimer, the term of this patent is extended or adjusted under 35 U.S.C. 154(b) by 691 days.

(21) Appl. No.: 11/607,624

(22) Filed: Nov. 30, 2006

(65) Prior Publication Data

US 2008/0132867 A1    Jun. 5, 2008

(51) Int. Cl.
*A61F 13/15* (2006.01)
*A61F 13/56* (2006.01)
*A61F 13/515* (2006.01)
*A61F 13/51* (2006.01)
*A61F 13/514* (2006.01)

(52) U.S. Cl.
CPC . *A61F 13/51405* (2013.01); *A61F 2013/51411* (2013.01); *A61F 13/5622* (2013.01); *A61F 13/515* (2013.01); *A61F 13/51478* (2013.01); *A61F 13/52* (2013.01); *A61F 13/51484* (2013.01); *A61F 13/51458* (2013.01)
USPC .......................................................... 604/389

(58) Field of Classification Search
CPC ............ A61F 13/514; A61F 13/51405; A61F 13/51458; A61F 13/51552; A61F 2013/51411; A61F 2013/51421
USPC ................................................ 604/389–391
See application file for complete search history.

(56) References Cited

U.S. PATENT DOCUMENTS

| | | | |
|---|---|---|---|
| 5,269,775 A * | 12/1993 | Freeland et al. | 604/385.22 |
| 5,718,698 A | 2/1998 | Dobrin et al. | |
| H0001952 H * | 3/2001 | Reed et al. | 604/391 |
| 6,482,191 B1 * | 11/2002 | Roe et al. | 604/385.01 |
| 6,677,258 B2 | 1/2004 | Carroll et al. | |
| 2002/0002359 A1 * | 1/2002 | Shingu et al. | 604/391 |
| 2003/0167049 A1 * | 9/2003 | Gibbs | 604/386 |

(Continued)

FOREIGN PATENT DOCUMENTS

| | | |
|---|---|---|
| JP | 63019505 A | 1/1988 |
| JP | 11244325 A | 9/1994 |

(Continued)

OTHER PUBLICATIONS

PCT/US/0784854ISR.

(Continued)

*Primary Examiner* — Lynne Anderson
(74) *Attorney, Agent, or Firm* — Amster, Rothstein & Ebenstein LLP

(57) ABSTRACT

An absorbent article is disclosed including a fluid and vapor pervious combination sheet having a shape defining a longitudinal axis, a minimum lateral dimension and a maximum lateral dimension, and a containment assembly having a shape defining a maximum lateral dimension which is less than the maximum lateral dimension of the combination sheet. The containment assembly includes a central, fluid permeable portion of the combination sheet; a fluid impermeable backing film disposed beneath the combination sheet; and an absorbent core sandwiched between the central portion of the combination sheet and the backing film. The containment assembly is integrally attached to the combination sheet along the longitudinal axis, and the combination sheet forms a plurality of breathable regions laterally disposed beyond the containment assembly. The backing film forms at least a portion of a stay away zone that resists engagement by the laterally disposed breathable regions.

43 Claims, 4 Drawing Sheets

(56) References Cited

U.S. PATENT DOCUMENTS

| | | | |
|---|---|---|---|
| 2005/0222546 A1* | 10/2005 | Vargo et al. | 604/361 |
| 2005/0256494 A1* | 11/2005 | Datta | 604/385.201 |
| 2005/0261650 A1 | 11/2005 | Damaghi et al. | |
| 2005/0277905 A1* | 12/2005 | Pedersen et al. | 604/389 |
| 2007/0049896 A1 | 3/2007 | Mills | |

FOREIGN PATENT DOCUMENTS

| | | |
|---|---|---|
| JP | 2002253608 A | 9/2002 |
| JP | 2004121363 A | 4/2004 |
| WO | 2005110310 A1 | 11/2005 |
| WO | 2006031670 A2 | 3/2006 |
| WO | PCT/US/0784854 | 11/2007 |

OTHER PUBLICATIONS

Chinese Office Action, corresponding to Chinese Patent Application No. 200780048477.5, mailed Apr. 23, 2012.

Japanese Office Action, corresponding to Japanese Patent Application No. 2009-539412, mailed May 8, 2012.

Supplemental European Search Report, corresponding to Application No. EP07854665, mailed May 16, 2012.

* cited by examiner

SKIN FRIENDLY DIAPER

FIELD OF THE INVENTION

The present invention relates generally to disposable absorbent garments such as disposable diapers, and more specifically to disposable diapers having stay away zones that have less affinity to engage hook-type and adhesive fasteners.

BACKGROUND OF THE INVENTION

Infants and other incontinent individuals wear disposable absorbent articles such as diapers to absorb and contain body exudates discharged from the body, particularly urine. Absorbent articles function to contain the discharged materials in isolation from the body of the wearer on one side, and from the wearers garments and/or bedding on the other. Absorbent articles are well known in the art and are typically constructed from a combination of liquid and vapor pervious and impervious materials which respectively allow the passage of liquid into the diaper and prevent its exit therefrom.

It is known to fasten a diaper about the body of a user using a variety of fasteners having a fastening material such as adhesive or a two part hook-and-loop type (i.e. Velcro). These fasteners are typically located at a front or rear portion of the diaper, such as a flap or wing, and are oriented to engage a "landing zone" on an opposing portion of the diaper. For an adhesive fastener, a release strip may be used as a landing zone; a Velcro fastener requires a special looped landing zone.

U.S. Published Patent Application No. US 2003/0004490 A1, issued to Larsson et al. discloses an absorbent article such as a diaper having a landing zone arranged on the front or rear portion of the product and at least one hook-bearing tab for detachable interaction with the landing zone. The landing zone includes both active areas, to which the tabs can be fastened, and inactive areas which will not adhere to the tabs. Particularly, the landing zone is a continuous support strip with an inactive area connected between two active areas. This enables two landing zones to be formed in one manufacturing step, from a single strip.

It is also known to make a diaper having Velcro-like hooks as one component of a fastening system and a nonwoven outer surface which serves as the other component. In such a diaper, the hook does not require a special landing zone having special loops. Instead, the entire outer surface of the diaper or brief can function as a landing zone for the hooks. This is known as a "loopless" fastening system, and provides an increased degree of flexibility in the fitting of a diaper to a person. Such a loopless fastener system is described in U.S. Patent Application Publication No. US 2003/0220626 A1 filed on May 7, 2003 and is hereby incorporated by reference.

Although such a loopless fastening system is more convenient for the user, there may be a tendency to take advantage of the unlimited landing area provided by loopless fasteners to use diapers that are not properly sized to the wearer. Particularly, diapers that are too large may still be nominally fitted to an individual due to the ability of the loopless fasteners to gather in the slack created by the oversized diaper. This practice is wasteful as larger diapers are likely to be more expensive, and require more material to manufacture.

U.S. Pat. No. 5,387,208 issued to Ashton et al. on Feb. 7, 1995 discloses an example of a diaper employing a plurality of layers of pervious, absorbent and impervious materials. Particularly, Ashton et al. discloses a pervious body facing top sheet and an impervious garment facing backsheet sandwiching a plurality of layers of variously liquid pervious and absorbent material. The liquid impervious backsheet extends beyond the dimension of the top and intervening layers, thereby providing laterally extending tabs which can be joined about the waist of the wearer to hold the diaper in place during use.

Although such backsheets do prevent liquid from passing through the diaper, the impervious nature of the backsheet, often a polyethylene film, also prevents the passage of air and water vapor, resulting in a diaper which can feel hot and uncomfortable to wear.

Backsheets which are pervious to vapor are generally known as breathable backsheets and have been described in the art. In general, these backsheets are intended to allow the passage of vapor through them while retarding the passage of liquid. For example, U.S. Pat. No. 3,156,242 issued to Crowe, Jr. on Nov. 10, 1964 teaches the use of a microporous film as a breathable backsheet. U.S. Pat. No. 3,881,489 issued to Hartwell on May 6, 1975 teaches a breathable backsheet having two layers, the first of which is a thermoplastic film and the second of which is a hydrophobic tissue.

While perforated backsheets may provide improved breathability over an impervious backsheet, the materials are of limited utility as they may require multiple layers of materials to prevent leakage. Fundamentally, perforation of otherwise impervious films achieves a measure of breathability at the expense of the material's ability to resist the flow of liquid, particularly when a diaper is subjected to the normal forces created by the wearer during use.

A modified approach is disclosed in U.S. Pat. No. 5,628,737 issued to Dobrin et al. on May 13, 1997, which provides a diaper having an impervious backsheet which extends laterally beyond the dimensions of the absorbent core and top sheet on the diaper wherein only the side panels are provided with perforation, thereby providing an impervious region adjacent to the core and a breathable region which permits some movement of vapor therethrough. This approach creates a zone of liquid impermeability where leaks would otherwise be most likely to occur in the backsheet, and provides a breathable region where leaks are less likely, e.g. where the backsheet comes in direct contact with the skin of the wearer.

Although the creation of zones of permeability in a diaper resolves some of the problems which are inherent to the backsheets of the prior art, the perforation of even an isolated region of a plastic film backsheet presents its own shortcomings, particularly due to the inherently impervious character of plastic film. For example, an impervious side panel having relatively large or many perforations may achieve the desired breathability, at the expense of the material strength in the perforated zone. Conversely, side panels having relatively few or small perforations may remain strong, yet provide insufficient breathability to ensure the comfort of the wearer. Basically, the shortcomings of the prior art stem from the attempt to make an impervious material selectively behave like a pervious material. Particularly, when this is attempted on a plastic film, the result cannot be accomplished without undermining the plastic film itself, where increased breathability comes at the expense of the material's desirable properties.

An additional disadvantage of the disposable diapers of the prior art is that extensive use of impervious material, typically plastic films, is environmentally detrimental as these films are known to be non-biodegradable. The introduction of perforations into otherwise impervious films as suggested in the prior art does not render these substances environmentally friendly. The environmental consequences are above and beyond the other economic disadvantages consequences of present diaper designs, particularly that the use of multiple layers of material and the application of the complex manufacturing techniques necessary in current diaper designs render these approaches more costly than necessary to manufacture and therefore less economical to purchase.

Finally, the use of a plastic film as a backsheet precludes the use of a loopless fastener system because a plastic film does not allow any use of the backsheet as a landing zone for a loopless fastener.

Another approach to creating a disposable absorbent article having breathable side panels is found in the Prevail® version of disposable protective underwear/briefs manufactured by First Quality Products, Inc. of McElhattan, Pa. The brief comprises a nonwoven pervious backsheet having an absorbent assembly attached thereto. The product crotch areas are provided with elastic bands sandwiched between the backsheet and an additional layer of nonwoven material. Thus, the side panels are generally pervious, although breathability is impeded by the multiple laminated nonwoven layers, and the adhesive that laminates them. This construction is similar to the Per-Fit® disposable breathable briefs, also manufactured by First Quality Products, Inc. which provides increased breathability in side panels comprising two laminated layers of nonwoven material, and is subject to the same drawbacks.

Copending U.S. application Ser. No. 10/841,119, filed May 7, 2004 and U.S. application Ser. No. 10/911,145, filed Aug. 4, 2004 disclose a diaper, having a liquid and/or vapor pervious backsheet formed of a single ply of material which extends laterally from a narrow fluid containment assembly having a liquid impervious backing film. The lateral extensions of the backsheet form a plurality of wings by which the absorbent article is secured about the body of a wearer, typically an infant. Although this design meets the need for an absorbent article such as a diaper having a fastening system which prevents improper sizing of oversized diapers, the complexity of the design introduces added costs.

Accordingly, a need exists for an absorbent article such as a diaper having a fastening system which prevents improper sizing of oversized diapers where said absorbent diaper can be produced in a simple and cost-effective manner.

A further need exists for an absorbent article such as a diaper having an absorbent core capable of absorbing and retaining fluids, while maximizing the breathability of the article.

A still further need exists for an absorbent article that minimizes the use of fluid impervious and/or non-biodegradable substances.

SUMMARY OF THE INVENTION

It is therefore a feature of various embodiments of the invention to address the aforementioned needs by providing a disposable absorbent article, such as a diaper, including a single layer, fluid and vapor pervious combination topsheet/backsheet ("combination sheet") having a shape defining a longitudinal axis, a minimum lateral dimension and a maximum lateral dimension, and a containment assembly having a shape defining a maximum lateral dimension which is less than the maximum lateral dimension of the combination sheet. The containment assembly includes a central, fluid permeable portion of the combination sheet; a fluid impermeable backing film disposed beneath the combination sheet; and an absorbent core sandwiched between the central portion of the combination sheet and the backing film. The containment assembly is integrally attached to the combination sheet along the longitudinal axis, and the combination sheet forms a plurality of single-layer fluid and vapor pervious regions laterally disposed beyond the containment assembly.

The backing film forms at least a portion of a stay away zone that resists engagement by fasteners attached to the laterally disposed regions.

These and other features of this invention are described in, or are apparent from, the following detailed description of various exemplary embodiments of this invention.

BRIEF DESCRIPTION OF THE DRAWINGS

Various exemplary embodiments of this invention will be described in detail, with reference to the following figures, wherein.

DESCRIPTION OF THE PREFERRED EMBODIMENTS

As used herein, the term "absorbent article" refers to devices which absorb and contain body exudates, and more specifically, refers to devices which are placed against or in proximity to the body of the wearer to absorb and contain the various exudates discharged by the body. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner. A "unitary" absorbent article refers to absorbent articles, such as diapers, which are formed of separate parts united together to form a coordinated entity so that they do not have multiple parts or require assembly prior to use such as a separate holder and liner.

Figure 1:
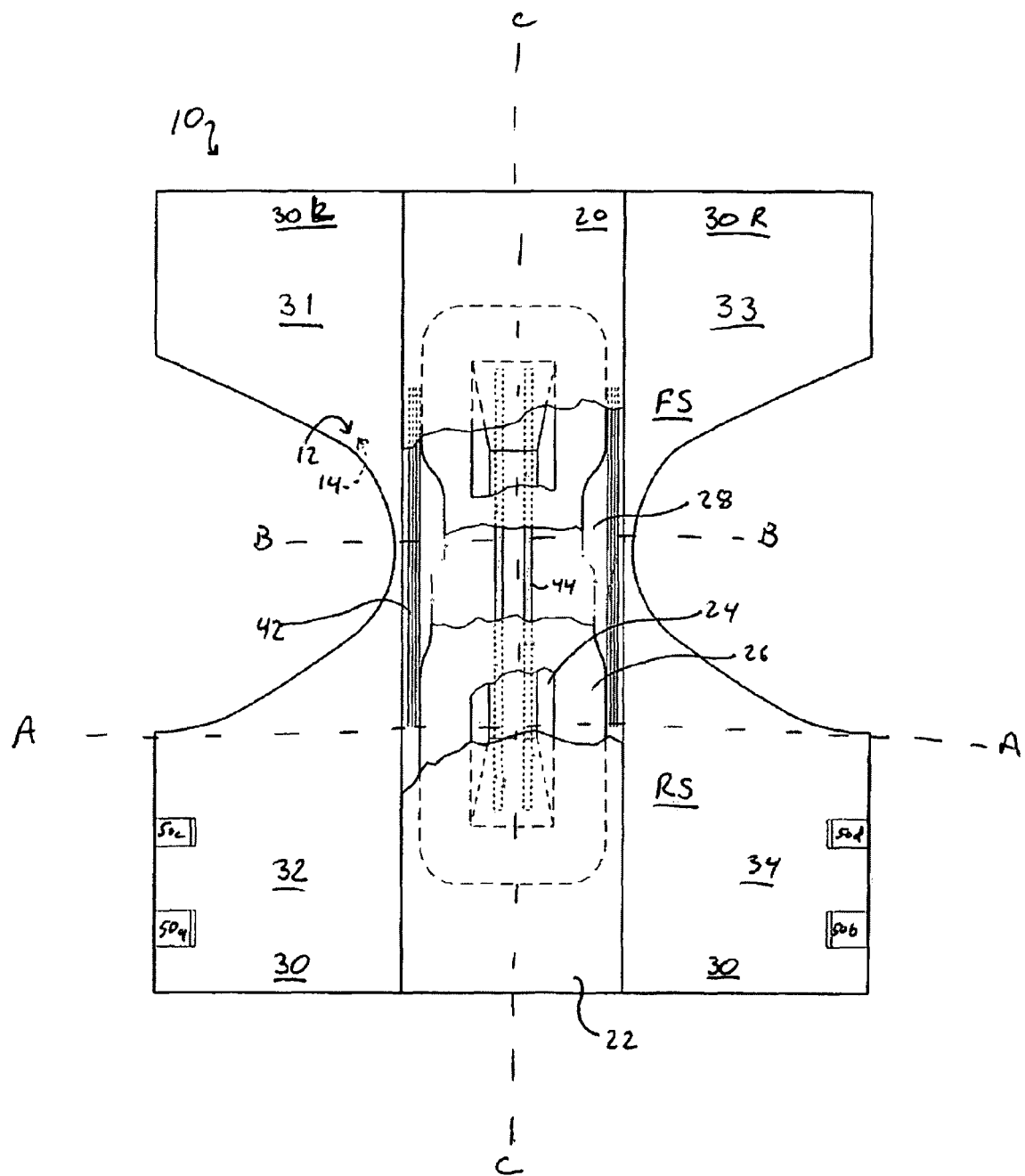
FIG. 1 is a plan view of an absorbent article according to an exemplary embodiment of the present invention.

A preferred embodiment of an absorbent article of the present invention is the unitary disposable diaper 10, shown in FIG. 1. As used herein, the term "diaper" refers to an absorbent article generally worn by infants and incontinent persons that is worn about the lower torso of the wearer. It should be understood, however that the present invention is also applicable to other absorbent articles such as incontinent briefs, incontinent undergarments, training pants, diaper holders, and panty liners and other feminine hygiene products. In particular, training pants or adult underwear have side panels which are pre-attached (using, for example, side seals) whereas ordinary diapers have wings which are fastened together to secure the diaper.

FIG. 1 is a plan view of the diaper 10 of the present invention, with elastic induced contraction pulled out, with a portion of the structure cut away to reveal the inner construction of diaper 10, and with body-facing side 12 facing upwardly. Diaper 10 has a longitudinal axis defined by longitudinal centerline C, the term "longitudinal", as used herein, referring to a line, axis or direction in the plane of diaper 10 that is generally aligned with, or parallel to, longitudinal centerline C and defines the length of diaper 10. Transverse axis B extends through diaper 10, intersecting longitudinal centerline C at a right angle in the plane of diaper 10. Transverse axis B defines the transverse orientation relative to diaper 10 and divides diaper 10 into front and rear sections FS and RS respectively. As used herein, the term "transverse" refers to a line, axis or direction that is generally perpendicular to the longitudinal direction and defines the width of diaper 10.

The perimeter of diaper 10 is defined by combination sheet 30 which performs the functions of both a topsheet and backsheet. The diaper 10 can be divided into three regions: a containment assembly 20 which extends symmetrically along longitudinal centerline C, and two longitudinally disposed portions 30L and 30R which extend variably in the transverse direction along their length and which define the left and right sides of the diaper respectively. In its preferred embodiment, combination sheet 30 of diaper 10 has an "hourglass" configuration wherein portions 30L and 30R narrow to form a crotch region at transverse axis B between front and rear sections FS and RS.

Figure 2:
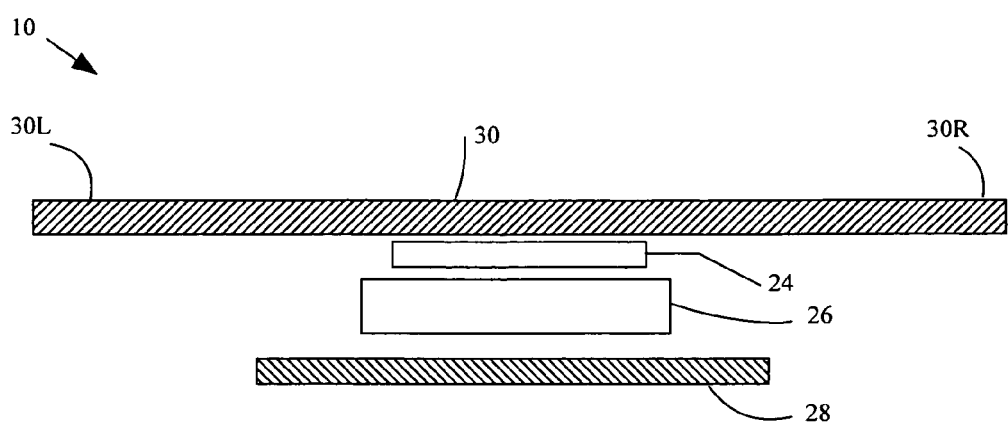
FIG. 2 is a lateral cross-sectional schematic of the absorbent article of FIG. 1 at line A-A.

Referring to FIGS. 1 and 2, the structure of diaper 10 is illustrated from body-facing surface 12 toward garment or outer surface 14. Containment assembly 20 preferably comprises a central portion 22 of combination sheet 30, an acquisition layer 24, an absorbent core 26 and a backing film 28. In a preferred embodiment, crotch elastic bands 42 and/or wetness indicators 44 may be added to one of the components of containment assembly 20. Containment assembly 20 is integrally attached to combination sheet 30 to form diaper 10.

Combination sheet 30 may be made of any suitable relatively liquid-pervious material currently known in the art or later discovered that permits passage of a liquid therethrough. Examples of suitable materials include nonwoven, spunbonded or carded webs of polypropylene, polyethylene, nylon, polyester and blends of these materials perforated, apertured or reticulated films, and the like. Nonwoven materials are exemplary because such materials readily allow the passage of liquids to the underlying acquisition layer 24, and therethrough to absorbent core 26. The combination sheet is preferably formed of a single ply of nonwoven material that may be made of thermally bonded, spunbond fibers, a spunbond-meltblown-spunbond composite or fibers that have been hydroentangled, having a basis weight of 5-45 grams per square meter and having appropriate strength and softness for use in an application which will be in contact with human skin. The central portion 22 of combination sheet 30 may be treated with surfactant, rendering it hydrophilic to facilitate the passage of moisture through central portion 22 and into the interior of containment assembly 20. Unlike central portion 22, the material used for the remainder of combination sheet 30 is preferably rendered hydrophobic by omitting the surfactant discussed above with respect to central portion 22. The present invention is not intended to be limited to any particular material for combination sheet 30 and other sheet materials will be readily apparent to those skilled in the art.

A preferred nonwoven material for use as combination sheet 30 is a nonwoven made from thermally bonded, spunbond fibers using a non-symmetrical pattern of fusion bonds (that is, an anisotropic or asymmetrical pattern) as disclosed in U.S. Pat. Nos. 6,537,644, 6,610,390, and 6,872,274, each of which is incorporated herein by reference. Preferably, the combination sheet 30 with a non-symmetrical pattern of fusion bonds has a basis weight of about 8-50 grams per square meter. Combination sheet 30, or a portion thereof, may also be treated with a surfactant to make it softer and more condrapable, such a finish being disclosed in U.S. Pat. No. 6,632,385, the contents of which are incorporated herein by reference. Particularly in the case, but not limited to, when combination sheet 30 is made from a material that is not innately hydrophobic, a surface treatment may be applied to improve the hydrophobic properties of the areas of combination sheet 30 other than central portion 22.

Acquisition layer 24 may be a single layer or multiple layers made of synthetic or natural material, or a combination of both, or a single multilayer apertured film. Acquisition layer 24 serves to quickly collect and distribute discharged body fluid to absorbent core 26. Because such fluid is typically discharged in gushes, the area of absorbent core 26 proximate to the point of fluid discharge may be overwhelmed by its rate, resulting in a leak. Therefore, the acquisition layer 24 facilitates transport of the fluid from the point of discharge across its surface area to contact other parts of absorbent core 26 from which it can be more readily absorbed. The use of an acquisition layer is well known in the art. Accordingly, acquisition layer 24 of diaper 10 of the present invention may have any well known or as yet undiscovered composition. Alternatively, absorbent core 26 may have the construction disclosed in U.S. Pat. No. 6,068,620 or U.S. Pat. No. 6,646,180 to Chmielewski, both of which are hereby incorporated by reference.

Absorbent core 26 may be any absorbent material which is generally compressible, conformable to the shape of the wearer's body and will not impede normal movement by the wearer, and capable of absorbing and retaining liquids such as urine and certain other body exudates. The absorbent core 26 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles such as wood pulp fluff. Examples of other suitable absorbent materials include creped cellulose wadding; meltblown polymers; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of absorbent core 26 may also be varied (e.g., the absorbent core may have varying caliper zones, a hydrophilic gradient, an absorbent gelling material gradient, or lower average density and lower average basis weight acquisition zones; or may comprise one or more layers or structures, i.e., members, including sheets or webs. In addition, each member need not be formed of a single unitary piece of material, but may be formed of a number of smaller strips or components joined together lengthwise or width-wise, as long as they are in fluid communication with one another.) The total absorbent capacity of absorbent core 26 should, however, be compatible with the design loading and the intended use of the diaper 10. Further, the size and absorbent capacity of the absorbent core 26 may be varied to accommodate wearers ranging from infants through adults.

Backing film 28 preferably is made from any suitably pliable liquid impervious material known in the art. Typical backing film materials include films of polyethylene, polypropylene, polyester, nylon and polyvinyl chloride and blends of these materials. For example, backing film 28 can be made of a polyethylene film having a thickness in the range of 0.5 to 2.0 mils. Other backing film materials will be readily apparent to those skilled in the art. Backing film 28 preferably has sufficient liquid imperviousness to prevent any leakage of fluids. The required level of liquid imperviousness may vary between different locations on diaper 10. Accordingly, the backing film 28 may be made vapor pervious or multi-layered, having varying degrees of liquid-imperviousness. Backing film 28 may have the same width as the central portion 22 of combination sheet 30, or may be narrower or wider. Preferably, central portion 22 and backing film 28 have about the same widths. Backing film 28 may be a composite of a film and another fibrous woven or nonwoven that is, for example, spunbond, melt blown, spunbond-meltblown-spunbond, thermally bonded or chemically bonded. These nonwovens may have very light to moderate bonding. For example, the cross direction tensile strength of each nonwoven may be less than 300 grams/inch, and preferably less than 100 grams/inch, so that hooks have relatively less affinity to attach to the backing film 28.

As discussed above, central portion 22, acquisition layer 24, absorbent core 26 and backing film 28 form the basic components necessary to the preferred embodiment of containment assembly 20. Crotch elastic bands 42 may be adhered to the lateral margins of containment assembly 20 to bias containment assembly 20 into a shape which conforms to that of the wearer's body. Furthermore, wetness indicators 44 may be provided in contact with absorbent core 26 to provide a visual indication that diaper 10 has received and is holding liquid. Suitable structures for the containment assembly 20 are disclosed in, for example, U.S. Patent Application Publication Nos. 20050261649, 20050267429 and 20060095012, the contents of which are incorporated herein by reference.

The width of the backing film 28 depends on the largest width and length of the absorbent core 26. For example, the width and length of the film backing 28 may be at least equal to the largest width and length of the core 26. Preferably, the film backing 28 is at least 0.5 inch larger than the largest width and length of the core 26. The width of the film backing 28 also depends on the diaper size. For example, in a medium size brief which is recommended for people having a 33 to 44 inch waist size, the width of the film backing 28 is preferably 15 inches, and in an extra-large size brief which is recommended for people having a 56-64 inch waist, the width of the backing film 28 is preferably 10-28 inches. Backing film 28 is preferably at least 0.5 inch wider and longer than the absorbent core 26 width and length, respectively, to prevent leakage of fluid from the absorbent core 26.

As shown in FIG. 1, containment assembly 20 is preferably, integrally attached to combination sheet 30 symmetrically along longitudinal centerline C. As containment assembly 20 is necessarily narrower and preferably shorter than at least some portions of combination sheet 30, portions of combination sheet 30 extend beyond containment assembly 20. In the preferred embodiment, the hourglass shape of combination sheet 30 results in two wings in each of longitudinal portions 30L and 30R extending beyond containment assembly 20.

Alternatively, a T-shaped combination sheet would result in one such wing in each of L and R respectively. Wings 31 and 33 are on front section FS of diaper 10 and wings 32 and 34 on rear section RS thereof. As each of wings 31-34 are formed of marginal portions of combination sheet 30, they comprise a single layer of liquid and vapor pervious material that is at least 0.5 inch wider and longer than absorbent core 26, rear wings 32 and 34 being provided with fasteners 50a-50d.

Figure 4:
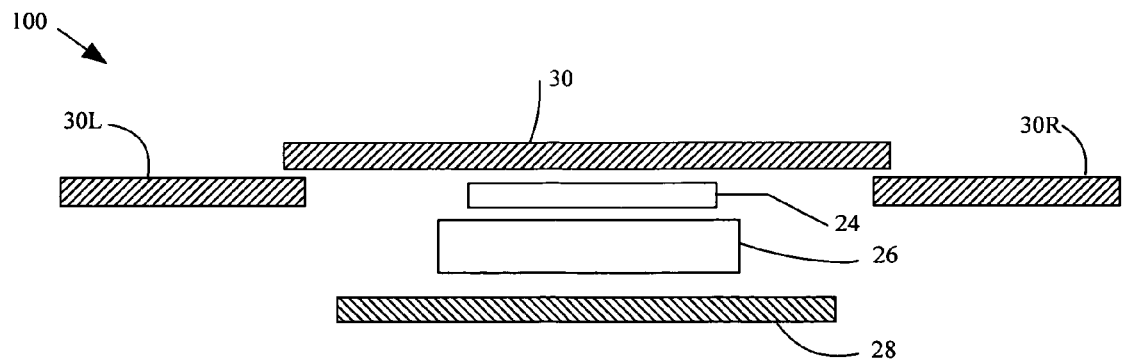
FIG. 4 is a lateral cross-sectional schematic of the absorbent article of FIG. 1 at line A-A according to another exemplary embodiment of the present invention.
Figure 5:
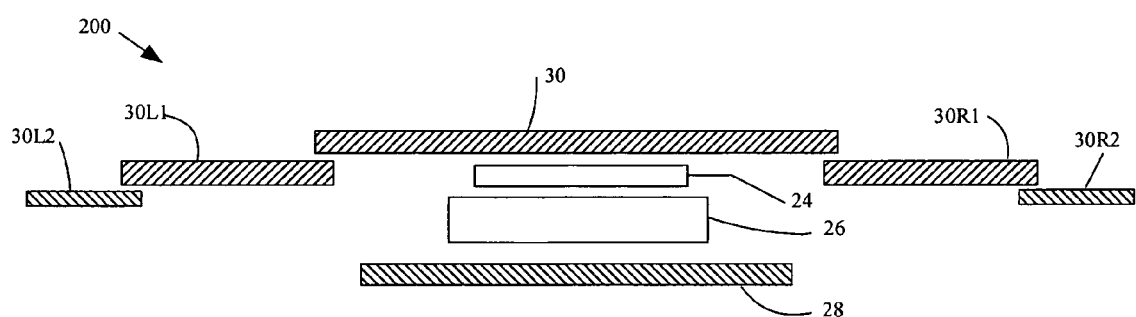
FIG. 5 is a lateral cross-sectional schematic of the absorbent article of FIG. 1 at line A-A according to another exemplary embodiment of the present invention.

Longitudinal portions 30L and 30R may each be made of one or two pieces and be attached to and extend from combination sheet 30, but are preferably formed integrally with combination sheet 30. FIG. 4 is a cross sectional view of a unitary disposable diaper, generally designated by reference number 100, according to an exemplary embodiment of the present invention in which longitudinal portions 30L and 30R are separate elements attached to the central nonwoven 30. The central nonwoven 30 may have a lower basis weight than separate longitudinal portions 30L and 30R. FIG. 5 is a cross sectional view of a unitary disposable diaper, generally designated by reference number 200, according to another exemplary embodiment of the present invention including longitudinal portions 30L and 30R, each including two separate portions 30L1 and 30L2, and 30R1 and 30R2, respectively, attached to the central nonwoven 30. The basis weight of portions 30R2 and 30L2 may be higher than the basis weight of portions 30R1 and 30L1.

The fasteners 50a-d may be any of adhesive, hook-and-loop, loopless or any other fastener known in the art which is capable of being secured, preferably removably, to the material of combination sheet 30. Suitable fastener constructions are described in, for example, U.S. Patent Application Publication Nos. 20030220626, 20040039364, 20030078558, 20050154366 and 20060058772, the contents of which are incorporated herein by reference.

It is known in the art to provide fasteners which have one end coated with a pressure sensitive adhesive. In a case where fasteners 50a-50d are formed of such pressure adhesive material, landing zones (not shown) are provided on the opposite side of the diaper corresponding to the location at which the fasteners are expected to be attached during assembly of the diaper. In this case, the landing zones may be a coated release paper or similarly smooth surface disposed over the nonwoven combination sheet 30. Similarly, a hook-and-loop type arrangement requires fasteners 50a-50d to have a plurality of either hooks or loops disposed on one side thereof, with a landing zones providing corresponding loops or hooks located respectively in corresponding regions on the opposite side of the diaper. The need for landing zones is a result of the fact that nonwoven material may not form a sufficiently strong bond with adhesive or other conventional fasteners to support the assembled diaper during use.

The need to provide a landing zone has been eliminated, however, by the introduction of minihook fasteners which are capable of fastening securely to conventional nonwovens without a corresponding landing zone. These loopless fasteners are ideal for providing a degree of flexibility and choice to the user in the positioning of the fasteners on the diaper.

A problem recognized with the loopless fastener, however, is that the flexibility they provide encourage the use of inappropriately sized diapers, for example a large diaper on a medium sized person, with the fasteners merely being secured to a more remote portion of the nonwoven outer surface of the diaper. This type of misuse is wasteful and could not occur in diapers requiring a landing zone as the landing zones limit the areas on the diaper to which a fastener can be applied.

To ameliorate this type of misuse, a stay away zone 100 could be provided on a portion of the outer surface of the diaper. The stay away zone could be limited to the most remote areas, thereby permitting a wide range of fastener placement while preventing improper sizing of the diaper. In at least one embodiment, since mini-hook fasteners do not attach to the backing film 28 of the containment assembly 20, the stay away zone 100 is formed by the backing film 28. Thus, a user is prevented from attaching the fasteners 50a-d to the backing film 28. Since it is highly desirable for the outer surface of the backing film 28 to be cloth-like, the backing film 28 may be coated with fibers such that the hooks may engage the backing film 28, but with a very low shear strength. For example, the fasteners may engage the backing film 28 with a shear strength that is 50% less than the shear strength associated with engagement of the fasteners with the nonwoven combination sheet 30. Also, powders, such as chuck, clay and ash having micron-sized or nano-sized particles may be laminated to the backing film 28 to make the backing film 28 surface non-film like to the touch so as to provide a cloth-like feel.

In other embodiments, the backing film 28 may form a portion of the stay away zone 100, and other portions of the stay-away zone may be created by spraying a solution or attaching a film (in addition to the backing film 28) over a portion of nonwoven combination sheet 30. Alternately, the stay away zone 100 could be extended beyond the backing film 28 by selectively modifying areas of nonwoven combination sheet 30, such as by heat or compression, to destroy its ability to adhere to the hooks of a loopless fastener.

Figure 3:
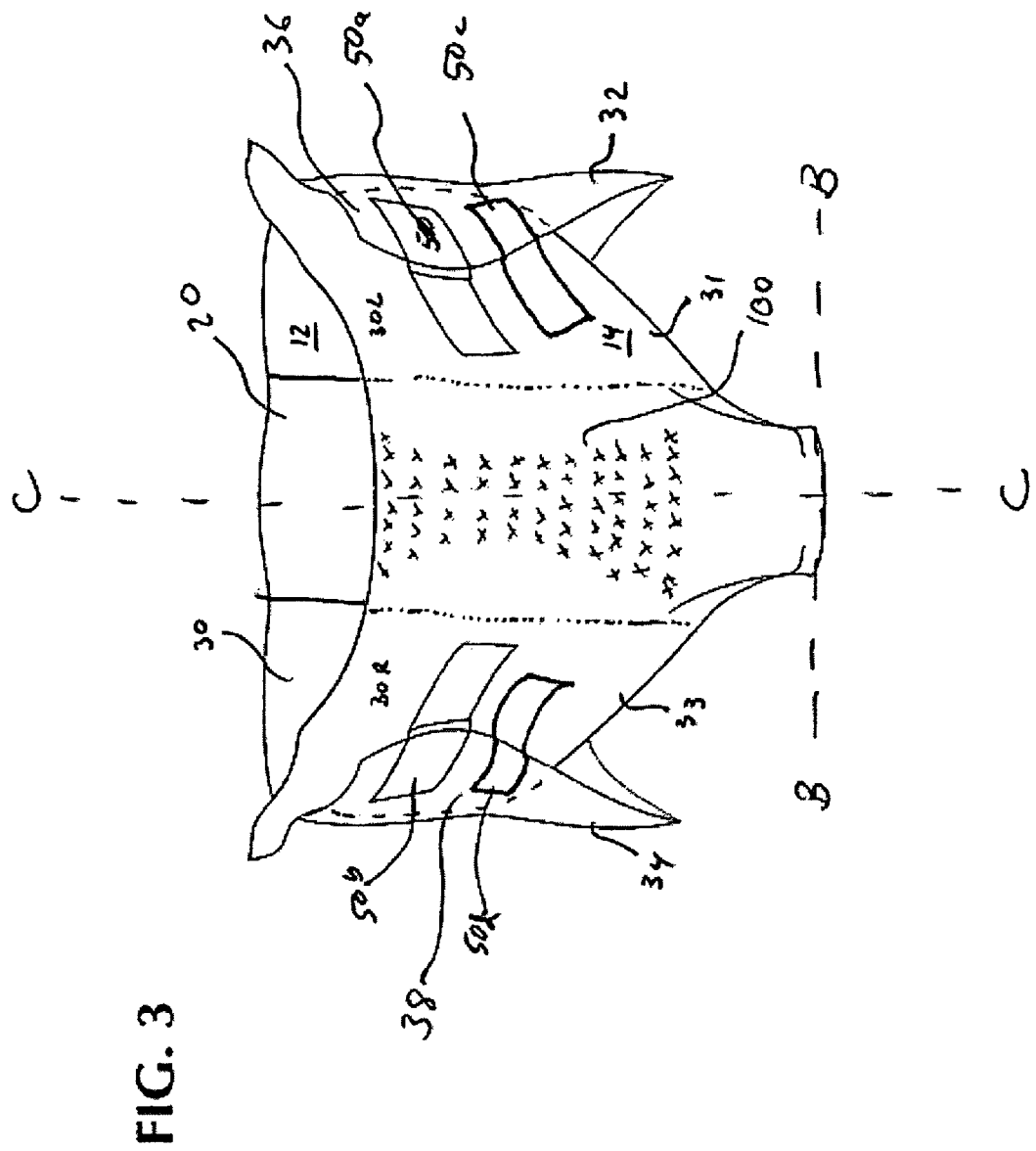
FIG. 3 is a perspective view of the absorbent article of FIG. 1 assembled for use.

As shown in FIG. 3, diaper 10 is shown as assembled. The diaper 10 is folded about lateral axis B as it would be about a wearer, such that body facing side 12 is oriented inward and outer surface 14 is oriented outward. Containment assembly 20 is shown between left and right longitudinal portions L and R which define the breathable portions of diaper 10 respectively. Specifically, on the right, wing 32 is shown folded over wing 31 and fastened thereto by fasteners 50*a* and 50*c*, creating overlapping region 36. Similarly, wing 34 is shown folded over wing 33 and fastened thereto by fasteners 50*b* and 50*d*, creating overlapping region 38. Thus, at the regions of diaper 10 defined by longitudinal portions L and R, only a single layer of liquid and vapor permeable material contact the skin of the wearer, with the exception of overlapping regions 36 and 38, which are similarly permeable. Thus, a diaper 10 is provided having breathable sides which increase the comfort of the diaper to the wearer.

Further, as shown in FIG. 3, the stay-away zone 100 formed by the backing film 28 at least over the central portion 22 of the combination sheet 30 prevents the fasteners 50*a-d* from attaching to the combination sheet 30. Thus, the diaper 10 is prevented from being misused by, for example, placement of a large size onto a medium sized person.

Additionally, due to the reduced size of impervious backing film 28 relative to combination sheet 30, a reduced amount of film material is required in the construction of diaper 10 relative to a diaper having an impervious backsheet. As backing film 28 is typically plastic and therefore non-biodegradable, the present invention provides a diaper with a minimum of such material.

In alternative embodiments of the present invention, the backing film 28 may be liquid and vapor permeable, resulting in a diaper that is fully breathable.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a vapor and fluid pervious combination sheet having a shape defining a longitudinal axis, a minimum lateral dimension and a maximum lateral dimension; and
a containment assembly having a shape defining a maximum lateral dimension which is less than the maximum lateral dimension of the combination sheet, the containment assembly comprising;
a central portion of the combination sheet;
a fluid impermeable backing film disposed beneath the central portion of the combination sheet; and
an absorbent core sandwiched between the central portion of the combination sheet and the backing film;
wherein the containment assembly is integrally attached to the combination sheet along the longitudinal axis, the combination sheet forming a single-layer comprising fluid and vapor pervious and hydrophobic outer regions laterally disposed beyond the containment assembly and a hydrophobic inner region disposed between the hydrophobic outer regions at the central portion of the combination sheet, wherein the laterally disposed outer regions are provided with fasteners for securing the absorbent article to the body of a wearer and the backing film forms at least a portion of a stay away zone that resists engagement by said fasteners, and the hydrophobic outer regions are more hydrophobic than the hydrophobic inner region.

2. The absorbent article of claim 1, wherein the shape of the containment assembly is generally symmetrical about a longitudinal axis.

3. The absorbent article of claim 2, wherein the central portion of the combination sheet of the containment assembly is attached to at least a portion of the backing film.

4. The absorbent article of claim 1, wherein a length and a width of the backing film are each at least 0.5 inch greater than a length and a width of the absorbent core.

5. The absorbent article of claim 2, wherein the containment assembly comprises elastic members.

6. The absorbent article of claim 2, wherein an acquisition layer is positioned between the central portion of the combination sheet and the absorbent core to facilitate distribution of moisture across the absorbent core.

7. The absorbent article of claim 1, wherein the central portion of the combination sheet is treated with a surfactant to render the central portion hydrophilic.

8. The absorbent article of claim 7, wherein the combination sheet is formed of a spunbond nonwoven and first ends of the fasteners are removably attachable thereto without adhesive.

9. The absorbent article of claim 8, wherein second ends of the fasteners are permanently attached to the combination sheet by ultrasonic/heat bonding.

10. The absorbent article of claim 8, wherein the combination sheet defines a front region at one end of the longitudinal axis and a rear region at the other end of the longitudinal axis, and a crotch region joining the front and rear regions, wherein the front and rear regions have a lateral dimension of approximately the maximum lateral dimension, and the crotch region has a lateral dimension of approximately the minimum lateral dimension.

11. The absorbent article of claim 10, wherein the maximum lateral dimension of the containment assembly does not exceed the minimum lateral dimension of the combination sheet.

12. The absorbent article of claim 1, wherein the laterally disposed regions and the central portion are individual elements longitudinally attached together to form the combination sheet.

13. The absorbent article of claim 12, wherein the laterally disposed regions have a higher basis weight than that of the central portion.

14. The absorbent article of claim 1, wherein each of the fasteners are permanently attached at one end to a first part of the combination sheet and have a fastening material at a second end thereof, the fastening material adapted to removably engage a second part of the combination sheet.

15. The absorbent article of claim 14, wherein the combination sheet is formed of nonwoven material and the fastening material is adapted to directly engage the nonwoven material.

16. The absorbent article of claim 14, wherein the combination sheet is formed of an apertured film.

17. The absorbent article of claim 15, wherein the combination sheet is formed of a hydroentangled, spunbond nonwoven.

18. The absorbent article of claim 15, wherein the combination sheet is a spunbond nonwoven.

19. The absorbent article of claim 15, wherein the central portion of the combination sheet is apertured.

20. The absorbent article of claim 15, wherein the stay away zone further comprises at least a portion of the combination sheet altered to resist engagement by the fastening material.

21. The absorbent article of claim 15, wherein the stay away zone further comprises at least a portion of the combination sheet covered by a material that resists engagement by the fastening material.

22. The absorbent article of claim 17, wherein the backing film is formed of a composite of nonwoven material and film so that the backing film has relatively less affinity to attach to hooks than the combination sheet.

23. A unitary disposable diaper having breathable side panels comprising:
   a vapor and fluid pervious combination sheet having a longitudinal axis defining a front portion at a first end of the longitudinal axis and a rear portion at a second end of the longitudinal axis connected by a crotch portion between the front portion and the rear portion, the combination sheet having a maximum lateral dimension at each of the front and rear portions thereof and having a minimum lateral dimension at the crotch region;
   a containment assembly having a shape defining a maximum lateral dimension which is less than the maximum lateral dimension of the combination sheet, the containment assembly comprising;
      a central, fluid pervious portion of the combination sheet;
      a fluid impermeable backing film disposed beneath the central portion of the combination sheet; and
      an absorbent core sandwiched between the central portion of the combination sheet and the backing film;
   wherein the containment assembly is integrally attached to the combination sheet such that the containment assembly does not extend laterally beyond the combination sheet, the combination sheet forming a single layer comprising fluid and vapor pervious and hydrophobic outer regions laterally disposed beyond the containment assembly and a hydrophobic inner region disposed between the hydrophobic outer regions at the central portion of the combination sheet, the laterally disposed outer regions comprising one or more fasteners and being fastenable to each other to form the breathable side panels, the backing film forming at least a portion of a stay away zone that resists engagement by the fasteners of the laterally disposed regions, and the hydrophobic outer regions are more hydrophobic than the hydrophobic inner region.

24. The unitary disposable diaper of claim 23, wherein the backing film is vapor permeable.

25. The unitary disposable diaper of claim 23, wherein the backing film is vapor impermeable.

26. The unitary disposable diaper of claim 23, wherein each of the fasteners is attached at one end to a first part of the combination sheet and has a fastening material at a second end thereof, the fastening material adapted to removably engage a second part of the combination sheet.

27. The unitary disposable diaper of claim 26, wherein the combination sheet is formed of nonwoven material and the fastening material is adapted to directly engage the nonwoven material.

28. The unitary disposable diaper of claim 16, wherein the combination sheet is formed of a hydroentangled, spunbond nonwoven.

29. The unitary disposable diaper of claim 28, wherein the nonwoven is apertured.

30. The unitary disposable diaper of claim 27, wherein the combination sheet is a spunbond nonwoven.

31. The unitary disposable diaper of claim 30, wherein at least a portion of the nonwoven is apertured.

32. The unitary disposable diaper of claim 27, wherein the stay away zone further comprises at least a portion of the combination sheet altered to resist engagement by the fastening material.

33. The unitary disposable diaper of claim 27, wherein the stay away zone further comprises at least a portion of the combination sheet covered by a material that resists engagement by the fastening material.

34. The unitary disposable diaper of claim 23, wherein the combination sheet is formed of a single layer of spunbond nonwoven material.

35. The unitary disposable diaper of claim 34, wherein apertures are formed in the central portion of the combination sheet.

36. The unitary disposable diaper of claim 23, wherein the containment assembly is generally rectangular, having a longitudinal dimension approximately equal in length to the longitudinal axis.

37. The unitary disposable diaper of claim 36, wherein the central portion of the combination sheet has a lateral dimension slightly wider than that of the backing film, and wherein the central portion of the combination sheet is attached to the backing film with the absorbent core positioned therebetween.

38. The unitary disposable diaper of claim 23, wherein the backing film is composed of a plurality of layers of vapor permeable material.

39. The unitary disposable diaper of claim 23, wherein the backing film is perforated.

40. The unitary disposable diaper of claim 39, wherein the backing film is formed of a composite of a nonwoven and a film so that the backing film has relatively less affinity to attach to hooks than the combination sheet.

41. The unitary disposable diaper of claim 23, wherein the laterally disposed regions and the central portion are individual elements longitudinally attached together to form the combination sheet.

42. The unitary disposable diaper of claim 41, wherein the laterally disposed regions have a higher basis weight that that of the central portion.

43. The unitary disposable diaper of claim 23, wherein a length and a width of the backing film are each at least 0.5 inch larger than a length and a width of the absorbent core.

* * * * *